(12) United States Patent
Lahtinen

(10) Patent No.: US 6,966,877 B2
(45) Date of Patent: Nov. 22, 2005

(54) METHOD AND DEVICE FOR MEASURING TRANSEPIDERMAL WATER LOSS OF SKIN SURFACE

(75) Inventor: Aulis Tapani Lahtinen, Kuopio (FI)

(73) Assignee: Delfin Technologies Ltd., Kuopio (FI)

( * ) Notice: Subject to any disclaimer, the term of this patent is extended or adjusted under 35 U.S.C. 154(b) by 156 days.

(21) Appl. No.: 10/144,358

(22) Filed: May 14, 2002

(65) Prior Publication Data

US 2002/0137992 A1    Sep. 26, 2002

Related U.S. Application Data

(63) Continuation of application No. PCT/FI00/01002, filed on Nov. 16, 2000.

(30) Foreign Application Priority Data

Nov. 16, 1999    (FI) .................................. 19992457

(51) Int. Cl.[7] .............................................. A61B 5/00
(52) U.S. Cl. ...................................... 600/307; 600/306
(58) Field of Search ................................ 600/307, 306, 600/300, 346, 353, 354, 357, 358, 363, 573; 73/29.01

(56) References Cited

U.S. PATENT DOCUMENTS

| | | |
|---|---|---|
| 3,914,982 A | 10/1975 | Zanetti |
| 4,066,068 A | 1/1978 | Nilsson et al. |
| 4,461,303 A | 7/1984 | Rofojo et al. |
| 4,607,719 A * | 8/1986 | Rugis et al. ................. 180/272 |
| 4,697,450 A | 10/1987 | Bachman et al. |
| 5,131,390 A * | 7/1992 | Sakaguchi et al. .......... 600/346 |
| 6,287,255 B1 * | 9/2001 | Endo et al. .................. 600/307 |
| 6,439,028 B1 * | 8/2002 | Imhof ........................ 73/29.01 |

FOREIGN PATENT DOCUMENTS

| | | |
|---|---|---|
| EP | 421 625 | 4/1991 |
| FI | 981295 | 12/1999 |

OTHER PUBLICATIONS

JP 1238824 A (Suzuken: Kk) Sep. 25, 1989 (Abstract). [on line] [retrieved on Feb. 15, 2001]. Retrieved from: EPO PAJ Database.

\* cited by examiner

Primary Examiner—Robert L. Nasser
Assistant Examiner—Navin Natnithithadha
(74) Attorney, Agent, or Firm—Pillsbury Winthrop Shaw Pittman LLP

(57)    ABSTRACT

A method for measuring the degree of evaporation of water through the skin includes placing a measurement chamber on the surface of the skin. The measurement chamber is a chamber which is open only at one side, and when placed on the skin it will become a totally closed chamber. During the measurement the vapor pressure is determined only in one point of the chamber. The degree of evaporation is determined by vapor pressure gradient in relation to time. An apparatus includes the measurement chamber open only at one side, and when placed on the skin it will become a totally closed chamber. Furthermore, there is a humidity sensor in the measurement chamber for measuring the vapor pressure in one point of the measurement chamber.

7 Claims, 2 Drawing Sheets

METHOD AND DEVICE FOR MEASURING TRANSEPIDERMAL WATER LOSS OF SKIN SURFACE

CROSS REFERENCE TO RELATED APPLICATIONS

This application is a continuation of PCT/FI00/01002, filed Nov. 16, 2000, which designated the United States. The entire contents of PCT/FI/01002 are incorporated herein by reference.

BACKGROUND OF THE INVENTION

1. Field of the Invention

The present invention relates to a method and an apparatus for measuring the degree of evaporation of water vapour passing through the skin, in which method a measurement chamber is placed on the surface of skin. The apparatus comprises a measurement chamber placed on the surface of the skin.

2. Description of the Related Art

The skin consists of three main layers, which are stratum corneum, epidermis and dermis. The water content is low in stratum corneum and high in dermis. The water content increases gradually from the surface of epidermis to deeper parts of epidermis. Water vapour diffuses continuously through the skin, because vapour pressure is higher in the dermis than in the external environment. Besides the external humidity, the amount of water vapour passing through the skin depends on the properties of the surface layer of the skin. The skin's function is to protect the human body against e.g. hazardous microbes and maintain the fluid balance of the body. Measuring the evaporation through the skin is an effective tool for the assessment of skin condition.

The devices for measuring the amount of water vapour passing through the skin are called TEWL meters (TEWL=transepidermal water loss). The well known TEWL meters, Evaporimeter from Servo Med (described in the U.S. Pat. No. 4,066,068) and DermaLab from Cortex Technology, are based on a technology where two humidity sensors are fitted in a chamber which is open at both ends. The probe is placed on the skin so that one open end is against the skin and the other open end is left in free contact with the ambient air. Due to the diffusion of water molecules from the skin, the humidity near the skin surface increases and becomes higher than the humidity of the ambient air. This creates a humidity gradient in the chamber. Two measuring sensors inside the chamber measure this humidity gradient. The humidity flow evaporated through the skin surface can be calculated by diffusion equations from the measured humidity gradient.

The drawback of these devices is that they are prone to disturbances caused by ambient airflows Disturbing ambient airflows can be generated e.g. by opening and closing the door or by some other airflow during the measurement.

The patent application FI-981295 describes a method for determining the diffusion flow of moisture to or from the surface of material. In this method a diffusing chamber is formed on the surface to be measured which is situated at the first end of the chamber, and the vapour pressure is determined or assumed to be known at least at two separate points of the chamber The diffusing chamber has another surface that evaporates or binds water vapour, from or into which the moistness is transferred during the measurement. The measuring time is typically approximately 15 minutes. This method is primarily meant for measuring moistness in constructions, and it is neither applicable nor practical for the measurement of water evaporation through skin.

SUMMARY OF THE INVENTION

The object of the invention is to provide a method and an apparatus for measuring transepidermal evaporation through the skin, which method and apparatus will obviate the shortcomings of the present methods and apparatus. It is a particular object of the invention to provide a method and an apparatus which are not sensitive to ambient airflows and with which reliable measurements can be done.

The object of the invention is achieved with method and apparatus that are characteristic of what is described in the claims.

In a method in accordance with the invention the measurement chamber is open only at one side, and when it is placed on the skin the measurement chamber will become a totally closed chamber. During the measurement the vapour pressure is determined only in one point of the chamber and the degree of evaporation is determined by the vapour pressure gradient in relation to time When this kind of measurement chamber is placed on the skin, the humidity inside the chamber starts to increase, and the amount of water vapour passing through the skin can be calculated from the gradient of humidity. The method is not sensitive to disturbances caused by ambient airflows, because the chamber is closed during the measurement. Furthermore, when the vapour pressure is measured only at one point and the degree of evaporation is determined by vapour pressure gradient in relation to time, the measurement results are obtained quickly, simply and reliably.

In an advantageous application of the invention the measuring time is short, preferably about 10–60 seconds. When the measuring time is short the results are obtained quickly and reliably.

In a further advantageous application of the invention the gradient of the vapour pressure is calculated from the beginning of the change, at which the so-called initial slope of the output of the humidity sensor is used in the calculation where the initial slope refers to the change in the output of the humidity sensor in relation to time right at the beginning of the measurement. Then the increase in the humidity inside the chamber does not affect the result, in consequence of which the measurement is quick and reliable.

In the apparatus according to the invention the measurement chamber is open only at one side, while placed on the skin it will become a totally closed chamber, and in the measurement chamber there is a humidity sensor for vapour pressure measurement in one point of the measurement chamber. Thus in this respect the apparatus differs from former devices and is also more simple and less expensive than former devices.

In an advantageous application of the apparatus in accordance with the invention the walls of the measurement chamber are made of dense material, which does not bind or release moisture The dense material suitable for the purpose is, for instance, preferably hard plastics. Thus the apparatus differs from the former device based on closed chamber and is also less expensive and easier to make.

BRIEF DESCRIPTION OF THE DRAWINGS

The invention will now be described in greater detail with reference to the accompanying drawings, where.

DETAILED DESCRIPTION

Figure 1:
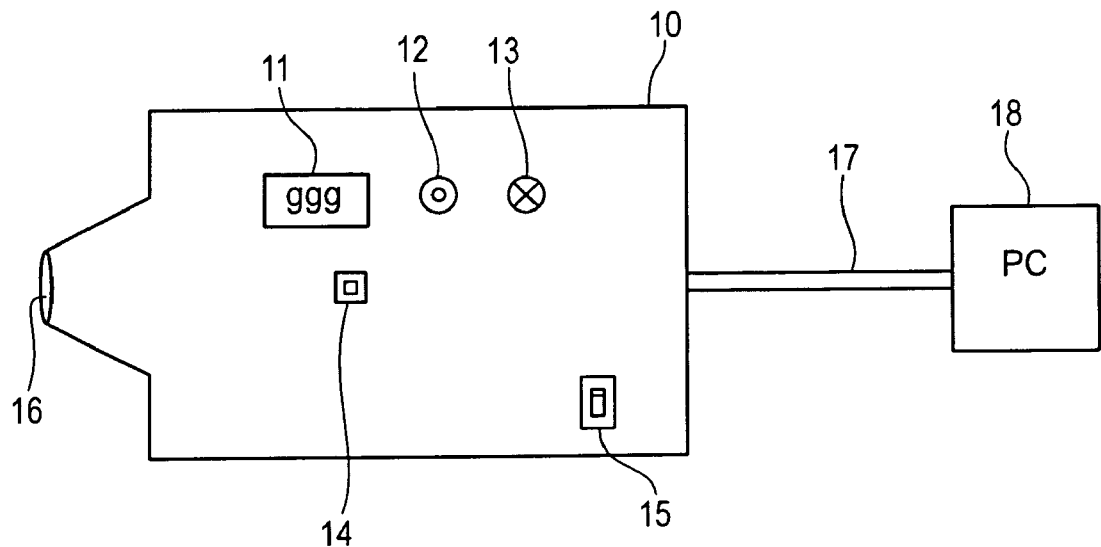
FIG. 1 shows the general view of an apparatus in accordance with the invention as seen from above.

FIG. 1 shows the case of the apparatus 10 and attached to it a display unit 11, a press button 12, an indicator light 13, a reset button 14 and an on-off switch 15. In one end of the case is the open end 16 of the measurement chamber. A cable 17 goes from the case to a computer 18. The shape, the structure of the case and the parts attached to it may differ in different applications of the invention.

Figure 2:
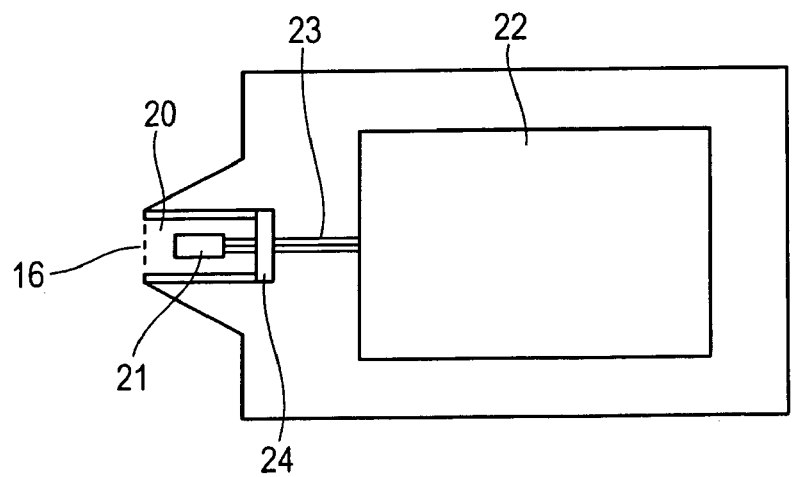
FIG. 2 shows the longitudinal cross-sectional view of an apparatus.

FIG. 2 shows a measurement chamber 20 having its one end 16 open. In the chamber has been placed a humidity measuring sensor 21 which is connected to a circuit card 22 in such a way that the wires 23 from the sensor 21 to the circuit card 22 go through the end wall 24 of the chamber.

Figure 3:
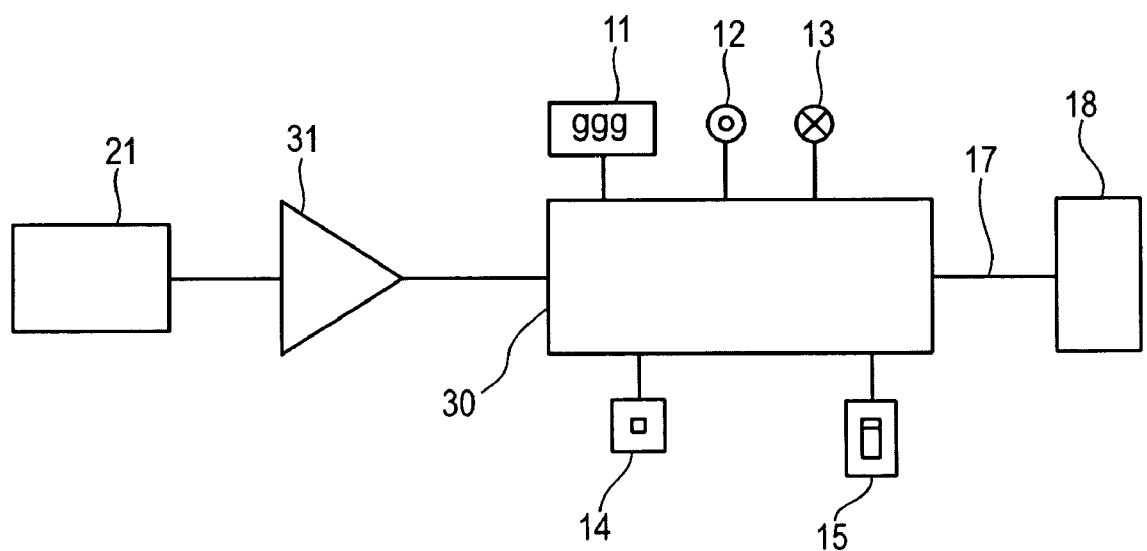
FIG. 3 shows a block diagram illustrating the function of the apparatus.

FIG. 3 shows a humidity sensor 21 which is connected to a digital electronic unit 30 through an operational amplifier 31. The display unit 11, the press button 12, the indicator light 13, the reset button 14, the switch 15 and the cable 17 to the computer 18 are connected to the digital electronic unit.

In using the apparatus it is set to operate by a switch 15 in either short or long measuring time. The short measuring time is about 15 seconds and the long time is about one minute. The short measuring time is used if the degree of evaporation is normal or higher than normal, and a longer measuring time is used when the evaporation rate is low. In this way the accuracy of measurement is high in every situation. The apparatus can be used either with computer connection or without computer connection operating with batteries.

In using the apparatus the button 12 is pressed at the same time when the opening 16 of the chamber in the apparatus is placed in contact with the skin. The measurement starts and during the measurement the apparatus registers the increase of the humidity in the chamber. The indicator light 13 is on during the measurement. The light 13 goes off and the buzzer (not in the figures) in the apparatus gives a short sound, indicating that the measurement is completed. After this, a reading which proportional to the degree of evaporation, appears in display 11. Pressing the reset button 14 will reset the display. However it is not necessary to reset the display between the measurements.

The digital electronic unit 30 of the apparatus calculates the degree of evaporation in the measurement chamber 20 from the slope of the measured humidity versus time.

The present invention is not restricted to the described advantageous application, but it can be embodied in other forms in the limits of the inventional idea defined by the claims.

What is claimed is:

1. An apparatus for measuring the degree of evaporation of water vapour through the skin, comprising:
    a measurement chamber to be placed on the skin, wherein the measurement chamber is open only at one side, and when placed on the skin becomes a totally closed chamber; and
    a humidity sensor in the measurement chamber for measuring the vapour pressure in one point of the measurement chamber.

2. An apparatus according to claim 1, wherein the walls of the measurement chamber are made of dense material, which does not bind or release moisture.

3. An apparatus according to claim 1, wherein the measurement chamber comprises one chamber.

4. A method for measuring the degree of evaporation of water vapour through the skin, comprising:
    providing a measurement chamber having on opening only at one side;
    placing the measurement chamber on the surface of skin to form a totally closed chamber;
    measuring the vapour pressure only one point of the chamber;
    determining the vapour pressure gradient in relation to time; and
    determining the degree of evaporation based on the vapour pressure gradient.

5. A method according to claim 4, wherein the measuring time is about 10–60 seconds.

6. A method according to claim 4 or 5, wherein the gradient of the vapour pressure is calculated from the beginning of a change in the measurement of the vapour pressure.

7. A method according to claim 4, wherein the measurement chamber comprises one chamber.

* * * * *